United States Patent [19]

Hammock et al.

[11] Patent Number: 5,445,956
[45] Date of Patent: Aug. 29, 1995

[54] RECOMBINANT SOLUBLE EPOXIDE HYDROLASE

[75] Inventors: Bruce D. Hammock; David F. Grant; Jeffrey K. Beetham, all of Davis, Calif.

[73] Assignee: The Regents of the University of California, Oakland, Calif.

[21] Appl. No.: 106,761

[22] Filed: Aug. 13, 1993

[51] Int. Cl.⁶ .......................... C12N 9/14; C12N 15/55
[52] U.S. Cl. .................................. 435/195; 435/320.1; 435/252.33; 435/240.2; 435/255.1; 536/23.2
[58] Field of Search ........................ 536/23.2; 435/69.1, 435/320.1, 252.33, 240.2, 255, 195, 255.1

[56] References Cited

PUBLICATIONS

Beetham et al (1993) Arch Biochem Biophys. 305(1), 197–201.
Maniatis et al (1982) in "Molecular Cloning: A Laboratory Manual" Cold Spring Harbor Laboratory pp. 404–433.
Silva et al (1987) Comp. Biochem Physiol 87B, 95–102.
Dietze et al. (1990) Int J. Biochem. 22, 461–470.
Wixtram et al. (1988) Anal. Biochem 169, 71–80.
Wozney et al. (1990) Meth Enzymol. 182, 738–749.
Arand et al (1991) FEBS Lett. 294, 19–22.
Cameron et al (1989) TIBTECH 7, 66–70.
Skoda et al. (1988) J. Biol Chem 263, 1549–1554.
Preprint, by Drs. Bruce Hammock and David Grant from Dr. Michael Arand. Author/Title: Knehr, Michael, Michael Arand, Thomas Gebel, Hans-Dieter Zeller, Helmut Thomas and Franz Oesch, Isolation and Characterization of a cDNA Encoding Rat Liver Cytosolic Epoxide Hydrolase.
Prestwich, Glenn D. and Bruce D. Hammock, Rapid purification of cytosolic epoxide hydrolase from normal and induced animals by affinity chromatography, *Proc. Natl. Acad. Sci.* 82:1663–1667 (1985).

*Primary Examiner*—Charles L. Patterson, Jr.
*Attorney, Agent, or Firm*—Townsend and Townsend Khourie and Crew

[57] ABSTRACT

The present invention relates to nucleic acid sequences and methods useful for producing recombinant human soluble epoxide hydrolase (sEH).

22 Claims, No Drawings

RECOMBINANT SOLUBLE EPOXIDE HYDROLASE

BACKGROUND OF THE INVENTION

The present invention relates to nucleic acid sequences and methods useful for producing recombinant human soluble epoxide hydrolase (sEH).

Epoxide hydrolases (EC 3.3.2.3) are a family of enzymes which hydrolyze a variety of exogenous and endogenous epoxides to their corresponding diols. Epoxide hydrolases have been found in tissues of all mammalian species tested. The highest levels of the enzyme were found in liver and kidney cells (see Wixtrom and Hammock *Pharmacology and Toxicology* (Zakim, D. and Vessey, D. A., ed.)1:1–93, Wiley, New York, 1985).

Four principal EH's are known, leukotriene epoxide hydrolase, cholesterol epoxide hydrolase, microsomal EH and sEH (previously called cEH). The leukotriene EH acts on leukotriene $A_4$, whereas the cholesterol EH hydrates compounds related to the 5,6-epoxide of cholesterol (Nashed, N. T., et al., *Arch. Biochem. Biophysics.*, 241:149–162, 1985; Finley, B. and B. D. Hammock, *Biochem. Pharmacol.*, 37:3169–3175,1988). The microsomal EH hydrates monosubstituted, 1,1-disubstituted, cis-1,2-disubstituted epoxides and epoxides on cyclic systems. The more abundant soluble EH hydrates a wide range of epoxides not on cyclic systems. The following schematic illustrates the hydrolysis of an epoxide to yield the vicinal product as catalyzed by sEH.

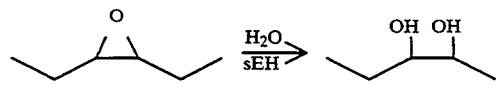

Compounds containing the epoxide functionality have become common environmental contaminants because of their wide use as pesticides, sterilants, and industrial precursors. Such compounds also occur as products, by-products, or intermediates in normal metabolism and as the result of spontaneous oxidation of membrane lipids (i.e. see, Brash, et.al., *Proc. Natl. Acad. Sci.*, 85:3382–3386 (1988), and Sevanian, A., et.al., *Molecular Basis of Environmental Toxicology* (Bhatnager, R. S., ed.) pp. 213–228, Ann Algor Science, Michigan (1980), which are incorporated herein by reference). As three-membered cyclic ethers, epoxides are often very reactive and have been found to be cytotoxic, mutagenic and carcinogenic (i.e. see Sugiyama, S., et.al., *Life Sci.* 40:225–231 (1987), which is incorporated herein by reference). Cleavage of the ether bond in the presence of electrophiles often results in adduct formation. As a result, epoxides have been implicated as the proximate toxin or mutagen for a large number of xenobiotics.

Soluble epoxide hydrolase as well as microsomal epoxide hydrolase metabolize a wide range of epoxides to their corresponding diols. Because of their broad substrate specificity these two enzymes are thought to play a significant role in ameliorating epoxide toxicity. Reactions of detoxification typically decrease the hydrophobicity of a compound, resulting in a more polar and thereby excretable substance. Soluble EH in human lymphocytes decreases the induction of sister chromatid exchanges by trans-β-ethylstyrene, an in vitro substrate of sEH (i.e. see Kramer, A., et.al., *Biochem. Pharmacol.* 42:2147–2152 (1991), incorporated herein by reference). Also, sEH of rodent decreased the mutagenicity of epoxide-containing compounds in the Ames' Salmonella assay (i.e. see El-Tantawy, M. A. and B. D. Hammock, *Mut. Res.* 79:59–71, which is incorporated herein by reference).

In addition to degradation of potential toxic epoxides, sEH are believed to play a role in the formation or degradation of endogenous chemical mediators. For instance, cytochrome P450 epoxygenase catalyzes NADPH-dependent enatioselective epoxidation of arachidonic acid to four optically active cis-epoxyeicosantrienoic acids (EETs) (Karara, A., et al., *J. Biol. Chem.*, 264:19822–19877, (1989)). Soluble epoxide hydrolase has been shown in vivo to convert these compounds with regio- and enantiofacial specificity to the corresponding vic-dihydroxyeicosatrienoic acids (DHETs). Both liver and lung cytosolic fraction hydrolyzed 14,15-EET, 8,9-EET and 11,12-EET in that order of preference. Purified sEH selected 8S,9R- and 14R,15S-EET over their enantiomers as substrates. Studies have revealed that EETs and their corresponding DHETs exhibit a wide range of biological activities. Some of these activities include involvements in luteinizing hormone-releasing hormone, stimulation of luteinizing hormone release, inhibition of $Na^+/K^+$ ATPase, vasodilation of coronary artery, mobilization of $Ca^{2+}$ and inhibition of platelet aggregation. Soluble epoxide hydrolase is believed to play a role in these biological activities by contributing to the regulation of the steady state levels of EETs and DHETs.

The sEH protein from human, rhesus monkey, baboon, rabbit, rat and mouse liver was affinity purified by Silva, M. H. and B. D. Hammock, *Comp. Biochem. Physiol.* 87B:95–102 (1987). The cDNA for human microsomal epoxide hydrolase has been cloned and expressed in COS-1 cells by Skoda, R. C., et. al., *J. Biol. Chem.*, 263:1549–1554 (1988). Although sEH of mouse, rat, and human have similar molecular weight and immunoreactivity as shown by Dietze, E. C., et. al., *Int. J. Biochem.*, 22:461–470 (1990), the data of Meijer, J. and J. W. Depierre, *Chem.-Biol. Interact.*, 64:207–249 (1988), suggest sEH of primates and non-primate species differ in substrate specificity and inhibition.

SUMMARY OF THE INVENTION

This invention provides for isolated DNA sequences encoding soluble epoxide hydrolase cloned from humans, Seq ID No.1, or from mouse, Seq ID No.3. The human or mouse sequences are capable of specifically hybridizing with either Seq ID Nos.1 or 3, respectively, under stringent conditions and in the presence of a corresponding human or mouse DNA sequence library. The isolated DNA sequence can be part of a recombinant vector and the recombinant vector can be capable of replicating in a prokaryotic or eukaryotic organism. Preferred prokaryotic organisms are *E. coli, Bacillus sp.,* or *Salmonella typhimurium*. Preferred eukaryotic organism cell lines are from yeast, insects, or mammals. Preferred mammalian cell lines are VERO, Hela, Chinese hamster ovary, WI38, BHK, COS, or MDCK. In addition, the isolated DNA sequence can be operably linked to an expression control sequence and contained in and expressed from an expression vector. The expression vector is capable of expressing the human sEH protein (Seq ID No.2) or mouse sEH protein (Seq ID No.4) in prokaryotes or eukaryotes. Prokaryotic expression is preferred in *E. coli, Bacillus sp.,* or *Salmonella typhimurium*. Eukaryotic expression is preferred in cell lines of yeast cells, insects cells, or mammalian cells.

For expression in mammalian cells, the cell lines VERO, Hela, Chinese hamster ovary, WI38, BHK, COS, or MDCK are preferred. For expression in insect cells the preferred cell line is *Spodoptera frugiperda* 21 (Sf21) and the expression vector is a recombinant *Autographa californica* nuclear polyhedrosis virus.

Another aspect of the invention are expression vectors that comprise an isolated DNA sequence encoding soluble epoxide hydrolase cloned from humans, Seq ID No.1, or from mouse, Seq ID No.3. The human or mouse sequences are capable of specifically hybridizing with either Seq ID Nos.1 or 3, respectively, under stringent conditions and in the presence of a corresponding human or mouse DNA sequence library.

A further aspect of the invention is a method of producing human or mouse soluble epoxide hydrolase protein, which comprises: (a) growing a culture of a microorganism harboring an expression vector having inserted therein an isolated DNA sequence encoding a human or mouse soluble epoxide hydrolase operably linked to an expression control sequence, said isolated DNA sequence specifically hybridizing to Seq ID No.1 or Seq ID No.3, respectively, and its corresponding gene under stringent conditions, said hybridization taking place in the presence of a human or mouse DNA sequence library, (b) expressing said soluble epoxide hydrolase from said expression vector, and recovering said protein therefrom. The method is capable of expressing the soluble epoxide hydrolase in a prokaryotic or eukaryotic organism. Preferred prokaryotic organisms are *E. coli, Bacillus sp.,* or *Salmonella typhimurium*. Preferred eukaryotic organism are cell lines from yeast, insects, or mammals. Preferred mammalian cell lines are VERO, Hela, Chinese hamster ovary, WI38, BHK, COS, or MDCK. In a further method, the sEH protein can be expressed in the preferred insect cell line *Spodoptera frugiperda* 21 (Sf21) with the expression vector being a recombinant *Autographa californica* nuclear polyhedrosis virus.

DETAILED DESCRIPTION

The invention relates to nucleic acid sequences that encode mammalian soluble epoxide hydrolase. In particular, the invention provides human and mouse nucleic acid sequences encoding sEH, expression vectors capable of expressing human and mouse sEH in different recombinant host cell systems, and methods for producing the recombinant human and mouse sEH. The sEH enzyme is then used to catalyze the hydrolysis of epoxides to the corresponding diol.

Definitions

"Nucleic acids", as used herein, may be DNA or RNA. Additionally, substantial nucleic acid sequence identity exists when a nucleic acid segment will hybridize, under stringent hybridization conditions, to a complement of another nucleic acid strand.

The phrase "nucleotide sequence" includes both the sense and antisense strands as either individual single strands or in the duplex.

The phrase "DNA sequence" refers to a single or double stranded DNA molecule composed of the nucleotide bases, adenosine, thymidine, cytosine and guanosine.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences includes both the full length nucleic acid sequences (Seq ID Nos.1 or 3) as well as non-full length sequences derived from the full length sequences. It being further understood that the sequence includes the degenerate codons of the native sequence or sequences which may be introduced to provide codon preference in a specific host cell.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

"Isolated" or "substantially pure" when referring to nucleic acid sequences encoding the sEH protein or fragments thereof refers to isolated nucleic acids which do not encode proteins or peptides other than sEH protein or peptides.

The term "recombinant" refers to DNA which has been isolated from its native or endogenous source and modified either chemically or enzymatically to delete naturally-occurring flanking nucleotides or provide flanking nucleotides that do not naturally occur. Flanking nucleotides are those nucleotides which are either upstream or downstream from the described sequence or sub-sequence of nucleotides.

The term "vector", refers to viral expression systems, autonomous self-replicating circular DNA (plasmids), and includes both the expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The phrase "selectively hybridizing to", refers to a nucleic acid that hybridizes duplexes or binds only to DNA sequences encoding one protein or portions thereof when the DNA sequences encoding the protein are present in a cDNA library. A DNA sequence which selectively hybridizes to a given target sequence can include sequences which are shorter or longer than the target sequence so long as they meet the functional test set forth. Hybridization conditions are specified along with the source of the cDNA library. Typically the hybridization is done in a Southern blot protocol using a 0.2×SSC, 0.1% SDS, 65° C. wash as described in examples 1 and 4 herein.

The term "SSC" refers to a citrate-saline solution of 0.15M sodium chloride and 20 mM sodium citrate. Solutions are often expressed as multiples or fractions of this concentration. For example, 6×SSC refers to a solution having a sodium chloride and sodium citrate concentration of 6 times this amount or 0.9M sodium chloride and 120 mM sodium citrate. 0.2×SSC refers to a solution 0.2 times the SSC concentration or 0.03M sodium chloride and 4 mM sodium citrate.

The term "plasmid" refers to an autonomous self-replicating circular DNA molecule and includes both the expression and nonexpression types. Where a recombinant microorganism or cell culture is described as hosting an "expression plasmid", this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

"Biological sample" refers to any sample obtained from a living organism or from an organism that has died. Examples of biological samples include body fluids and tissue specimens. In the case of microorganisms a biological sample may include samples containing many entire organisms.

The phrase "biologically pure" refers to material which is substantially or essentially free from components which normally accompany it as found in its native state. Thus, the sEH molecules of this invention do not contain materials normally associated with their in situ environment, e.g., other cytosolic or peroxisomal proteins. Even where a protein has been isolated to a homogenous or dominant band using standard electrophoretic techniques, there are trace contaminants in the range of 5-10% of native protein which co-purify with the desired protein. Biologically pure material does not contain such endogenous co-purified protein.

A. General Recombinant DNA Methods

This invention relies on routine techniques in the field of recombinant genetics. A basic text disclosing the general methods of use in this invention is Sambrook et al., *Molecular Cloning, A Laboratory Manual*, Cold Spring Harbor Publish., Cold Spring Harbor, N.Y. 2nd ed. (1989) and Kriegler, *Gene Transfer and Expression: A Laboratory Manual*, W. H. Freeman, N.Y., (1990), which are both incorporated herein by reference. Unless otherwise stated all enzymes are used in accordance with the manufacturer's instructions.

Nucleotide sizes are given in either kilobases (Kb) or base pairs (bp). These are estimates derived from agarose or acrylamide gel electrophoresis or from published DNA sequences.

Oligonucleotides that are not commercially available can be chemically synthesized according to the solid phase phosphoramidite triester method first described by S. L. Beaucage and M. H. Caruthers, *Tetrahedron Letts.*, 22(20):1859-1862 (1981), using an automated synthesizer, as described in D. R. Needham Van Devanter et. al., *Nucleic Acids Res.*, 12:6159-6168, 1984. Purification of oligonucleotides is by either native acrylamide gel electrophoresis or by anion-exchange HPLC as described in J. D. Pearson and F. E. Reanier, *J. Chrom.*, 255:137-149, 1983.

The sequence of the cloned genes and synthetic oligonucleotides can be verified using the chemical degradation method of A. M. Maxam et al., *Methods in Enzymology*, 65:499560, (1980). The sequence can be confirmed after the assembly of the oligonucleotide fragments into the double-stranded DNA sequence using the method of Maxam and Gilbert, supra, or the chain termination method for sequencing double-stranded templates of R. B. Wallace et al. *Gene*, 16:21-26, 1981. Southern Blot hybridization techniques are carried out according to Southern et al., *J. Mol. Biol.*, 98:503, 1975.

B. Cloning Methods for the Isolation of Nucleotide Sequences Encoding Soluble Epoxide Proteins In general, the nucleic acid sequences encoding SEH are cloned from DNA sequence libraries that are made to encode copy DNA (CDNA) or genomic DNA. The particular sequences can be located by hybridizing with an oligonucleotide probe, the sequence of which can be derived from Seq. I.D. Nos.: 1 or 3. The desired target sequences may also be obtained using polymerase chain reaction (PCR) primers which amplify either the entire gene, cDNA or portions there of. PCR primers can be selected from the sequences provided herein. Alternatively, where the sequence is cloned into an expression library, the expressed recombinant SEH can be detected immunologically with antisera or purified antibodies made against sEH.

To make the cDNA library, one should choose a source that is rich in mRNA. The mammalian liver is one such source. Dietze, E. C., et al, reported in *Int. J. Biochem.*, 22:461-470 (1990) that sEH mRNA is induced by peroxisome proliferators such as clofibrate (2-(4-Chlorophenoxy)-2-methylpropanoic acid ethyl ester). Typically, the mammal, as for example a mouse, is fed clofibrate for a period of time, its liver removed and mRNA extracted using standard techniques. The mRNA can then be made into cDNA, ligated into a recombinant vector, and transfected into a recombinant host for propagation, screening and cloning. Methods for making and screening cDNA libraries are well known. See Gubler, U. and Hoffman, B. J. *Gene* 25:263-269, 1983 and Sambrook.

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro, as described in Sambrook. Recombinant phage are analyzed by plaque hybridization as described in Benton and Davis, *Science*, 196:180-182 (1977). Colony hybridization is carried out as generally described in M. Grunstein et al. *Proc. Natl. Acad. Sci. USA.*, 72:3961-3965 (1975).

An alternative method combines the use of synthetic oligonucleotide primers with polymerase extension on an mRNA or DNA template. This polymerase chain reaction (PCR) method amplifies the desired nucleotide sequence. Restriction endonuclease sites can be incorporated into the primers. U.S. Pat. Nos. 4,683,195 and 4,683,202 describe this method. Genes amplified by the PCR reaction can be purified from agarose gels and cloned into an appropriate vector.

Synthetic oligonucleotides can be used to construct genes. This is done using a series of overlapping oligonucleotides usually 40-120 bp in length, representing both the sense and nonsense strands of the gene. These DNA fragments are then annealed, ligated and cloned.

The gene for sEH is cloned using intermediate vectors before transformation into mammalian cells for expression. These intermediate vectors are typically prokaryote vectors or shuttle vectors. The sEH protein can be expressed in either prokaryotes or eukaryotes.

C. Expression in Prokaryotes

To obtain high level expression of a cloned gene, such as those cDNAs encoding sEH in a prokaryotic system, it is essential to construct expression plasmids which contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky, C., *J. Bacteriol.*, 158:1018-1024

(1984), and the leftward promoter of phage lambda (P$_L$) as described by Herskowitz, I. and Hagen, D., *Ann. Rev. Genet.*, 14:399–445 (1980).

Expression systems for expressing the sEH protein are available using *E. coli, Bacillus sp.* and *Salmonella* (Palva, I et al., *Gene* 22:229–235 (1983); Mosbach, K. et al., *Nature*, 302:543–545 (1983).

The sEH protein produced by prokaryote cells will not be glycosylated and may not necessarily fold properly. During purification from *E. coli*, the expressed sEH protein may first be denatured and then renatured. This can be accomplished by solubilizing the bacterially produced proteins in a chaotropic agent such as guanidine HCl and reducing all the cysteine residues with a reducing agent such as beta-mercaptoethanol. The protein is then renatured, either by slow dialysis or by gel filtration. U.S. Pat. No. 4,511,503.

When expressing sEH protein in *S. typhimurium*, one should be aware of the inherent instability of plasmid vectors. To circumvent this, the foreign gene can be incorporated into a nonessential region of the host chromosome. This is achieved by first inserting the gene into a plasmid such that it is flanked by regions of DNA homologous to the insertion site in the Salmonella chromosome. After introduction of the plasmid into the *S. typhimurium,* the foreign gene is incorporated into the chromosome by homologous recombination between the flanking sequences and chromosomal DNA.

An example of how this could be achieved is based on the his operon of Salmonella. Two steps are involved in this process. Firstly, a segment of the his operon must be deleted in the Salmonella strain selected as the carrier. Secondly, a plasmid carrying the deleted his region downstream of the gene encoding the sEH protein is transformed into the his Salmonella strain. Integration of both the his sequences and the gene encoding the sEH protein occurs, resulting in recombinant strains which can be selected as his+.

Detection of the expressed protein is achieved by methods known in the art as radioimmunoassays, or Western blotting techniques or immunoprecipitation. Purification from *E. coli* can be achieved following procedures described in U.S. Pat. No. 4,511,503.

D. Expression in Eukaryotes

Standard eukaryotic transfection methods are used to produce mammalian, yeast or insect cell lines which express large quantities of sEH protein which are then purified using standard techniques. See, e.g., Colley et al., *J. Biol. Chem.* 264:17619-17622, (1989), and Guide to Protein Purification, in Vol. 182 of *Methods in Enzymology* (Deutscher ed., 1990), both of which are incorporated herein by reference.

Transformations of eukaryotic cells are performed according to standard techniques as described by D. A. Morrison, *J. Bact.*, 132:349-351 (1977), or by J. E. Clark-Curtiss and R. Curtiss, *Methods in Enzymology,* 101:347-362, Eds. R. Wu et. al., Academic Press, New York (1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see Sambrook et al., supra). It is only necessary that the particular genetic engineering procedure utilized be capable of successfully introducing at least one gene into the host cell which is capable of expressing the sEH protein.

The particular eukaryotic expression vector used to transport the genetic information into the cell is not particularly critical. Any of the conventional vectors used for expression in eukaryotic cells may be used. Expression vectors containing regulatory elements from eukaryotic viruses are typically used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A+, PMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

The vectors usually comprise selectable markers which result in gene amplification such as the sodium, potassium ATPase, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving gene amplification are also suitable, such as using a bacculovirus vector in insect cells, with the SEH encoding sequence under the direction of the polyhedrin promoter or other strong baculovirus promoters.

The expression vector of the present invention will typically contain both prokaryotic sequences that facilitate the cloning of the vector in bacteria as well as one or more eukaryotic transcription units that are expressed only in eukaryotic cells, such as mammalian cells. The vector may or may not comprise a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the transfected DNA integrates into the genome of the transfected cell, where the promoter directs expression of the desired gene. The expression vector is typically constructed from elements derived from different, well characterized viral or mammalian genes. For a general discussion of the expression of cloned genes in cultured mammalian cells, see Sambrook et al., supra, Ch. 16.

The prokaryotic elements that are typically included in the mammalian expression vector include a replicon that functions in *E. coli,* a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells.

The expression vector contains a eukaryotic transcription unit or expression cassette that contains all the elements required for the expression of the sEH DNA in eukaryotic cells. A typical expression cassette contains a promoter operably linked to the DNA sequence encoding a sEH protein and signals required for efficient polyadenylation of the transcript. The DNA sequence encoding the sEH protein may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens.* Additional elements of the cassette may include enhancers and, if genomic DNA is used as the structural gene, introns with functional splice donor and acceptor sites.

Eukaryotic promoters typically contain two types of recognition sequences, the TATA box and upstream promoter elements. The TATA box, located 25–30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, *Enhancers and Eukaryotic Expression,* Cold Spring Harbor Pres, Cold Spring Harbor, N.Y. 1983, which is incorporated herein by reference.

In the construction of the expression cassette, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

In addition to the elements already described, the expression vector of the present invention may typically contain other specialized elements intended to increase the level of expression of cloned genes or to facilitate the identification of cells that carry the transfected DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

After the expression vector is introduced into the cells, the transfected cells are cultured under conditions favoring expression of the sEH protein which is recovered from the culture using standard techniques 1. Expression in Yeast Synthesis of heterologous proteins in yeast is well known and described. *Methods in Yeast Genetics,* Sherman, F., et al., Cold Spring Harbor Laboratory, (1982) is a well recognized work describing the various methods available to produce sEH protein in yeast.

For high level expression of a gene in yeast, it is essential to connect the gene to a strong promoter system as in the prokaryote and also to provide efficient transcription termination/polyadenylation sequences from a yeast gene. Examples of useful promoters include GAL1,1O (Johnson, M., and Davies, R. W., *Mol. and Cell. Biol.,* 4:1440–1448 (1984)) ADH2 (Russell, D., et al., *J. Biol. Chem.,* 258:2674–2682, (1983)), PHO5 (*EMBO J.* 6:675–680, (1982)), and MFα1. A multicopy plasmid with a selective marker such as Leu-2, URA-3, Trp-1, and His-3 is also desirable.

The MFα1 promoter is preferred. The MFα1 promoter, in a host of the α mating-type is constitutive, but is switched off in diploids or cells with the a mating-type. It can, however, be regulated by raising or lowering the temperature in hosts which have a ts mutation at one of the SIR loci. The effect of such a mutation at 35° C. on an α type cell is to turn on the normally silent gene coding for the α mating-type. The expression of the silent a mating-type gene, in turn, turns off the MFα1 promoter. Lowering the temperature of growth to 27° C. reverses the whole process, i.e., turns the a mating-type off and turns the MFα1 on (Herskowitz, I. and Oshima, Y., in *The Molecular Biology of the Yeast Saccharomyces,* (eds. Strathern, J. N. Jones, E. W., and Broach, J. R., Cold Spring Harbor Lab., Cold Spring Harbor, N.Y., pp.181–209, (1982).

The polyadenylation sequences are provided by the 3′-end sequences of any of the highly expressed genes, like ADH1, MFα1, or TPI (Alber, T. and Kawasaki, G., J. of *Mol. & Appl. Genet.* 1:419–434, (1982).

A number of yeast expression plasmids like YEp6, YEp13, YEp4 can be used as vectors. A gene of interest can be fused to any of the promoters in various yeast vectors. The above-mentioned plasmids have been fully described in the literature (Botstein, et al., 1979, *Gene,* 8:17–24, (1979); Broach, et al., *Gene,* 8:121–133, (1979)).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, *Nature* (London), 275:104–109, (1978); and Hinnen, A., et al., *Proc. Natl. Acad. Sci. USA,* 75:1929–1933, (1978). The second procedure does not involve removal of the cell wall. Instead the cells are treated with lithium chloride or acetate and PEG and put on selective plates (Ito, H., et al., *J. Bact.,* 153:163–168, (1983)).

Soluble epoxide hydrolase protein can be isolated from yeast by lysing the cells and applying standard protein isolation techniques to the lysates. The monitoring of the purification process can be accomplished by using Western blot techniques or radioimmunoassays.

2. Expression in insect cells

The baculovirus expression vector utilizes the highly expressed and regulated *Autographa californica* nuclear polyhedrosis virus (AcMNPV) polyhedrin promoter modified for the insertion of foreign genes. Synthesis of polyhedrin protein results in the formation of occlusion bodies in the infected insect cell. The recombinant proteins expressed using this vector have been found in many cases to be, antigenically, immunogenically, and functionally similar to their natural counterparts. In addition, the baculovirus vector utilizes many of the protein modification, processing, and transport systems that occur in higher eukaryotic cells.

Briefly, the DNA sequence encoding sEH is inserted into a transfer plasmid vector in the proper orientation downstream from the polyhedrin promoter, and flanked on both ends with baculovirus sequences. Cultured insect cell, commonly *Spodoptera frugiperda*, are transfected with a mixture of viral and plasmid DNAs. The virus that develop, some of which are recombinant virus that result from homologous recombination between the two DNAs, are plated at 100-1000 plaques per plate. The plaques containing recombinant virus can be identified visually because of their ability to form occlusion bodies or by DNA hybridization. The recombinant virus is isolated by plague purification. The resulting recombinant virus, capable of expressing sEH, is self propagating in that no helper virus is required for maintenance or replication. After infecting an insect culture with recombinant virus, one can expect to find recombinant protein within 48-72 hours. The infection is essentially lytic within 4-5 days.

There are a variety of transfer vectors into which the sEH gene can be inserted. For a summary of transfer vectors see Luckow, V. A. and M. D. Summers, *Bio/Technology*, 6:47-55 (1988). Preferred is the transfer vector pAcUW21 described by Bishop, D. H. L. in *Seminars in Virology*, 3:253-264, (1992).

3. Expression in recombinant vaccinia virus-infected cells

The gene encoding sEH protein is inserted into a plasmid designed for producing recombinant vaccinia, such as pGS62, Langford, C. L., et al., *Mol. Cell. Biol.* 6:3191-3199, (1986). This plasmid consists of a cloning site for insertion of foreign genes, the P7.5 promoter of vaccinia to direct synthesis of the inserted gene, and the vaccinia TK gene flanking both ends of the foreign gene.

When the plasmid containing the sEH gene is constructed, the gene can be transferred to vaccinia virus by homologous recombination in the infected cell. To achieve this, suitable recipient cells are transfected with the recombinant plasmid by standard calcium phosphate precipitation techniques into cells already infected with the desirable strain of vaccinia virus, such as Wyeth, Lister, WR or Copenhagen. Homologous recombination occurs between the TK gene in the virus and the flanking TK gene sequences in the plasmid. This results in a recombinant virus with the foreign gene inserted into the viral TK gene, thus rendering the TK gene inactive. Cells containing recombinant viruses are selected by adding medium containing 5-bromodeoxyuridine, which is lethal for cells expressing a TK gene.

Confirmation of production of recombinant virus can be achieved by DNA hybridization using cDNA encoding the sEH protein and by immunodetection techniques using antibodies specific for the expressed protein. Virus stocks may be prepared by infection of cells such as HeLA S3 spinner cells and harvesting of virus progeny.

4. Expression in Cell Cultures

Soluble epoxide hydrolase cDNA can be ligated to various expression vectors for use in transforming host cell cultures. The vectors typically contain gene sequences to initiate transcription and translation of the sEH gene. These sequences need to be compatible with the selected host cell. In addition, the vectors preferably contain a marker to provide a phenotypic trait for selection of transformed host cells such as dihydrofolate reductase or metallothionein. Additionally, a vector might contain a replicative origin.

Cells of mammalian origin are illustrative of cell cultures useful for the production of the sEH. Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, COS-7 or MDCK cell lines.

As indicated above, the vector, e.g., a plasmid, which is used to transform the host cell, preferably contains DNA sequences to initiate transcription and sequences to control the translation of the sEH gene sequence. These sequences are referred to as expression control sequences. Illustrative expression control sequences are obtained from the SV-40 promoter (*Science,* 222:524–527, (1983)), the CMV I. E. Promoter (*Proc. Natl. Acad. Sci.* 81:659–663, (1984)) or the metallothionein promoter (*Nature* 296:39–42, (1982)). The cloning vector containing the expression control sequences is cleaved using restriction enzymes and adjusted in size as necessary or desirable and ligated with sequences encoding the sEH protein by means well known in the art.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., *J. Virol.* 45: 773–781, (1983)).

Additionally gene sequences to control replication in the host cell may be incorporated into the vector such as those found in bovine papilloma virus type-vectors. Saveria-Campo, M., "*Bovine Papilloma virus DNA a Eukaryotic Cloning Vector*" in DNA Cloning Vol. II a Practical Approach Ed. D. M. Glover, IRL Press, Arlington, Va. pp. 213–238, (1985).

The transformed cells are cultured by means well known in the art. For example, as published in *Biochemical Methods in Cell Culture and Virology,* Kuchler, R. J., Dowden, Hutchinson and Ross, Inc., (1977). The expressed sEH protein is isolated from cells grown as suspensions or as monolayers. The latter are recovered by well known mechanical, chemical or enzymatic means.

E. Protein Purification

Purification of sEH is obtained using methods known in the art. The recombinant cells are harvested and lysed or where cells are secreting sEH, the conditioned media is collected. The sEH is purified by way of affinity chromatography using derivatized epoxy-activated sepharose as described by Wixtrom, R. N., et al., *Anal. Biochem.*, 169:71–80 (1988) incorporated herein by reference. Preferred is epoxy-affinity activated Sepharose CL-6B derivatized with benzlthiol groups. To prepare the affinity matrices, Sepharose CL-6B is epoxy-activated and coupled to the various thiol ligands as described by Prestwich, G. D., et al., *Arch. Biochem. Biophys.*, 228:639–645 (1984); Porath, J. P., in *Methods in Enzymology* (Jakoby, W. B., and Wilchek, M. Eds.), Vol 34, Part B, pp. 13–30, (1974) Academic Press, New York, and Wixtrom supra, all of which are incorporated herein by reference.

F. Enzyme Assay

To detect soluble epoxide hydrolase activity or to monitor its relative purity, one uses the partition assay of Wixtrom, R. N., and B. D. Hammock in *Biochemical Pharmacoloyt and Toxicology* (Zakim, D., and Vessey, D. A., Eds), Vol. 1, pp. 1–93. Wiley, New York (1995) with [$^3$H]-trans-stilbene oxide ([$^3$H]TSO) as substrate, incorporated herein by reference. In brief this assay entails: coincubating the enzyme with radiolabled substrate that is much more soluble in organic than aqueous solutions. Next, the enzyme substrate is extracted with organic solvent such that the substrate partitions into the organic phase but the more polar and water-soluble product (a vicinal diol) partitions to the aqueous phase. An aliquot of the aqueous phase is then analyzed for concentration of product by quantification of radioactivity. The substrate [$^3$H]TSO is prepare by the method described by Gill, S. S., et al., in *Anal. Biochem.*, 131:273–282 (1993) incorporated herein by reference.

The following examples are offered by way of illustration, not by way of limitation.

EXAMPLES

Example 1. Cloning of Murine Soluble Epoxide Hydrolase a) cDNA Library Construction and Screening The sequence of the murine sEH cDNA is shown in the sequence listing as Seq ID No.3. The corresponding amino acid sequence is shown as Seq ID No.4. To clone and express this sequence, the following methods may be followed.

Total RNA is isolated, as described by Chomczynski and Sacchi, *Anal. Biochem.*, 162:156–159, (1987), from the livers of male Swiss Webster mice (Charles River) after treatment of the mice for 14 days with 0.5% w/w clofibrate (2-(4-Chlorophenoxy)-2-methylpropanoic acid ethyl ester) as described by Dietze et al., *Int. J. Biochem.*, 22:461–470, (1990). Poly(A+) RNA is selected by oligo(dT)-cellulose chromatography using an Invitrogen mRNA isolation kit. A cDNA library from the RNA of a single mouse is constructed using the 5' Eco RI and 3' Xho I cloning sites of the Uni-Zap ™ XR vector system from Stratagene according to the supplied protocol. Ideally, The phage library is plated as separate primary plaques that are easily isolated. The library screened with use of a murine sEH sequence hybridization probe.

The original sequences for the murine sEH were obtained using degenerate probes. With knowledge of the sequence disclosed herein, one can target select specific sequences for designing primers and probes for identifying and isolating the murine cDNA or gene.

The following primer pairs are used to PCR amplify target sEH sequences contained in the cDNA library. A primer pair to amplify the entire coding region is:

A. 5'-ATGGCGCTGCGTGTAGCCGCGTT-CGACCTT-3' (Seq ID No.5)
B. 5'-TGAGGTTTAGCTTTATTGAAT-GAAAATCTT-3' (Seq ID No.6)

A primer pair to amplify sequence that lies within the coding region is:

C. 5'-GCCCTGGCACTGC-CTAGAGACTTCCTGCTT-3' (Seq ID No.7)
D. 5'-AATCTTGGAGGTCACTGATGGGTTCT-GGAC-3' (Seq ID No.8)

Polymerase chain reaction conditions are as follows: 1 cycle of 3 min at 95° C., 5 min at 55° C., 40 s at 72° C.: 40 cycles of 40 s at 95° C., 1 min at 55° C., 2 min at 72° C.: 1 cycle of 40 s at 95° C., 1 min at 55° C., 5 min at 72° C.

The 5' ends of the primers may be designed to contain flanking restriction site sequences for cloning purposes. The amplified material can then be cloned into an sequencing vector such as M13 and sequenced by the dideoxy chain termination method of Sanger, et al., *Proc. Natl. Acad. Sci. U.S.A.*, 74:5463–5467, (1977).

To identify and isolate cDNA clones, the library is screened by plaque hybridization using the cloned amplified sequences as probes. The probe is radiolabled by as for example, using PCR as described by the method of Jansen and Ledley, *Gene Anal. Techn.*, 6:79–83, (1989). Sequencing of cloned inserts longer than 500–600 bases may be obtained by subcloning the insert as a series of unidirectional nested deletions using the Erase-a-Base ® system from Promega (Madison, Wis.) and sequencing by the dideoxy chain termination method of Sanger, supra.

b) Expression of murine sEH in COS-7 cells i) Expression Vector Construction

To express murine sEH, the expression vector pJ3omega is used. The pJ3omega expression vector is described by Morgenstern, J. P. and J. Land, in *Nucl. Acids Res.* 18:1068 (1990). To subclone the murine cDNA between the Xba I/Sac I sites of pJ3omega, an Spe I and an Sac I restriction site is added to the 5' and 3' ends respectively, of Seq ID No.3. The restriction sites are added to the sequence using PCR and primers that contain the appropriate restriction site sequence. The 5' primer would have the following sequence (Spe I site underlined):

5'GGACTAGTATGGCGCTGCGT-GTAGCCGCGTTCGACCTT-3' (Seq ID No.9)

The 3' primer would have the following sequence (Sac I site underlined):

5'GGGAGCTCTGAGGTTTAGCTTTATTGAAT-GAAAATCTT-3' (Seq ID No.10)

The sequence is PCR amplified, digested with Spe I and Sac I, agarose purified and subcloning into Xba I/Sac I digested pJ3omega to obtain the murine sEH-pJ3omega expression vector. Plasmid DNA use for transfections are purified by centrifugation on a cesium chloride, ethidium bromide equilibrium gradient (Sambrook et al., (1989)).

ii) COS-7 cell culture and detection of recombinantly expressed sEH cos-7 cells are grown as a monolayer culture in Dulbecco's modified Eagle's medium (ICN) containing 10% fetal calf serum (ICN) plus penicillin G (100 U/ml) and streptomycin sulfate (100 ug/ml). Cell transfections are mediated by lipofectin (Gibco) according to standard protocol. Approximately $1 \times 10^6$ cells are transfected in 100 mm dishes with 5 ug of murine sEH-pJ3omega, 5 ug pJ3omega vector control or a mock transfection control containing lipofectin only (60 ul/plate). All transfections except the mock transfection control contain 2.5 ug of the beta-galactosidase plasmid, pSV-beta-Gal (Promega) can be used as an internal positive control. After 36 hours, cells are washed 5 times with PBS and collected by scraping into 1.5 ml centrifuge tubes. The cells are then pelleted (12 k×g, 4° C., 30 seconds), resuspended in 150 ul of lysis buffer (40 mM tris, pH 8.0, 150 mM NaCl, 0.2 mM PMSF, 1 mM EDTA) and lysed by 3 cycles of freezing and thawing. The cells are again centrifuged and the supernatant used for enzyme assays and protein determination. Beta-galactosidase is assayed as described (Sambrook et al., 1989). sEH activity is assayed using TSO as described by the method of Wixtrom, R. N. and B. D. Hammock in Biochemical *Pharmacology and Toxicology*, (Zakim, D. and Vessey, D. A., ed.) 1:1–93 (1985).

In addition to measuring sEH enzyme activity in transiently transfected COS-7 cells, one can analyze the transfected COS-7 cell soluble protein from transfected COS-7 cells by immunoblotting for expression of sEH. Detection is done with antibodies developed in rabbits against both the murine sEH and the rhesus sEH. These antibodies are described by Silva, M. and B. D. Hammock, in *Comp. Biochem. Physiol.*, 87B:95–102 (1987). SDS electrophoresis is performed according to Laemmli, *Nature*, 227:680–685 (1970), using 3.3% stacking and 10% resolving gels. Molecular weight standards can be obtained from Bio-Rad (Richmond, Calif.). Immunoblotting is performed according to Burnette, W. N., in *Analyt. Biochem.* 112:195–203 (1981), using 0.2 um pore size nitrocellulose in a Bio-Rad mini trans-blot cell. After overnight transfer (35 V, room temperature), blots are blocked by shaking for 30 min in 50% calf serum (ICN, Costa Mesa, Calif.) 50% blotting buffer (10 mM KH$_2$PO$_4$, 14 mM NaCl, 0.25% tween-20, pH 7.4). Primary antiserum (1:5000) is added for 2 h with shaking a room temperature. Bound IgG is detected as described by Blake, M. S., et al., in *Analyt. Biochem.*, 136:175–179 (1984), using alkaline phosphatase labeled goat-anti-rabbit-IgG (1:2000 in blotting buffer, Sigma, St. Louis, Mo.). Protein concentrations are determined using the bicinchoninic acid reagent (Pierce, Rockford, Ill.) according to protocol directions using bovine serum albumin as standard.

iii) Functional analysis of recombinant murine sEH expressed in COS-7 cells

The functional analysis of recombinant murine sEH expressed in COS-7 cells was performed following the methods described above. The results in Table I show that after subtracting sEH activity not inhibited by the sEH inhibitor t-ENPG, cells transfected with the COS-7 expression vector psEH-2-pJ3 omega expressed approximately 5 to 10-fold more sEH activity than did the control expression vector that was minus sEH cDNA, pJ3 omega vector, transfected or mock transfected cells. Transfected cells expressed approximately the same level of sEH activity as did mock transfected cells when 1 mM t-ENPG was included in the enzyme assay. These results suggest that COS-7 cells have low but measurable basal sEH activity. The differences in specific activity among the experiments in Table I are most likely due to differences in cell density during transfections.

TABLE I

Expression of murine sEH enzyme activity in cell extracts of transfected COS-7 cells.

| Construct | Epoxide hydrolase activity[1] (±S.D.) | | |
|---|---|---|---|
| | Experiment 1 | Experiment 2 | Experiment 3 |
| psEH-pJ3omega | 550 ± 10 | 1100 ± 40 | 771 ± 13 |
| psEH-pJ3omega + t-ENPG[2] | 76 ± 20 | 109 ± 4 | 134 ± 6 |
| pJ3omega | 140 ± 1 | 212 ± 20 | 223 ± 5 |
| pJ3omega + t-ENPG | 69 ± 6 | 97 ± 4 | 113 ± 8 |
| Mock | 169 ± 7 | 206 ± 1 | 195 ± 13 |
| Mock + t-ENPG | 74 ± 6 | 106 ± 5 | 88 ± 2 |

[1] Data are expressed as pmol (min mg)$^{-1}$ and are the means of 3 replicates for each of the 3 independent experiments. Enzyme activities were within the linear range of the assay (as defined by Wixtrom and Hammock, supra).
[2] The sEH inhibitor used was trans-2(S),3(S)-epoxy-3-(4-nitrophenyl) glycidol purchased from Aldrich at 1 mM final concentration. This compound inhibits monkey and murine microsomal EH by ≦23% at 2 mM and soluble EH by ≧50% at 8 uM.

In addition to detecting sEH with an enzyme assay, immunoblotting was used to confirm the expression of murine sEH in the transfected COS-7 cells from experiments 2 and 3 in Table I. The results showed that the anti-mouse-sEH antiserum recognizes a band that migrates identically with purified mouse sEH and is only expressed in cells that were transfected with psEH-pJ3omega. These results support the conclusion that psEH-2 encodes a functional epoxide hydrolase. As well as detecting the transiently expressed sEH, the anti-rhesus-sEH antiserum also detected a protein that migrates identically with mouse sEH. This result is due to the fact that COS-7 cells are monkey kidney cells and the monkey antibody is picking-up basal levels of monkey sEH.

Example 2. Cloning and Expression of Human sEH a) cDNA Library Construction and Screening The sequence of the human sEH cDNA is shown in the sequence listing as Seq ID No.1. The corresponding amino acid sequence is shown as Seq ID No.2. In a manner similar to that described above for murine sEH, the human sequence can be cloned and express following the methods below.

A Uni-Zap TM cDNA library can be prepared by Stratagene from the liver of a human that has no apparent liver disorder. The library is plated on XL-1 Blue *E. coli* cells, and screened as described by Sambrook and the instructions supplied by Sratagene. The library is screened with use of a human sEH sequence hybridization probe. Positive plaques are isolated and inserts excised from clones by coinfecting XL1 Blue cells with Uni-Zap TM clones and R-408 helper phage. Excision results in formation of pBluescript SK plasmids containing the cloned DNA between the EcoR1 and XhoI polycloning sites. Cloned inserts are then characterized by restriction enzyme analysis, and the largest clone selected for sequencing. The sequence is verified by making deletion series subclones and sequencing both DNA strands. Any sequence compressions are resolved using dITP.

The following primer pairs are used to PCR amplify target human sEH sequences shown in Seq ID No.1 that are contained in the Uni-Zap TM cDNA library. Each primer contained a 5' 8 base region with an EcoRI or HindIII restriction enzyme site. A primer pair to amplify the entire coding region is:

E.                                           5'-CGGAATTCAT-GACGCTGCGCGGCGCCGTCTTCGACCTT-3' (Seq ID No.11)

F. 5'-CGAAGCTTGTAAGGCATC-
CCAATCTCTGCTAAGATTCT-3' (Seq ID No.12)

A primer pair to amplify sequence that lies within the coding region is:

G. 5'-CGGAATTCGACGGGGTGCTGGCGCTG-
CCAGCGGTGTTC-3' (Seq ID No.13)

H. 5'-CGAAGCTTCTACATCTTTGAGAC-
CACCGGTGGGTTCCG-3' (Seq ID No.14)

Suggested PCR conditions are: 1 cycle of 3 min at 95° C., 5 min at 55° C., 40 s at 72° C.: 40 cycles of 40 s at 95° C., 1 min at 55° C., 2 min at 72° C.: 1 cycle of 40 s at 95° C., 1 min at 55° C., 5 min at 72° C. The PCR products obtained are then extracted and precipitated, digested with EcoR1 and HindIII and separated on low melting temperature agarose. DNA bands are next cut out of the agarose, ligated into plasmid pUC118 (according to FMC recommended procedures) then electroporated into *Escherichia coli* for amplification of the plasmid. The pUC118 clones are verified by restriction enzyme analysis and sequenced by the dideoxy chain termination method of Sanger, supra.

As described above for the murine cDNA encoding sEH, amplified human sEH sequences can then be used to probe the Uni-Zap ™ cDNA library to detect and clone the cDNA encoding human sEH.

b) detection of human sEH mRNA

Total RNA is extracted from 1.09 grams of human liver and the poly(A)+ subfraction isolated by oligo-dT chromatography (FastTrack ™, Invitrogen). Messenger RNA (4.5 μg) is separated by electrophoresis on a 1.2% agarose-formaldehyde gel as described by Sambrook, electroblotted onto nitrocellulose, then fixed by exposure to ultraviolet light (Stratalinker ™, Stratagene). The blot is probed (as described for probing the cDNA library blots using a human sEH hybridization probe prepared as describe above and radiolabeled using PCR) and washed (0.2×SSC, 0.1% SDS, 60° C.). The blot is exposed at −70° C. to X-ray film with an intensifying screen.

The Northern blot analysis will show a single mRNA band of 2.0 kbase hybridizes to the human sEH cDNA probe. The deduced molecular weight of 62,640 is in close agreement with published values for purified monomer of non recombinant hsEH published by Wixtrom, R. N., et al., in *Anal. Biochem.*, 169:71–80 (1988) and by Chang, C. and S. S. Gill in *Arch. Biochem. Biophys.*, 285:276–284, (1991).

c) Expression of human sEH in Baculovirus system

A baculovirus transfer vector containing human sEH cDNA is constructed as follows; A mutated pBluescript plasmid containing an extra EcoRI restriction site (such that the polycloning site was ordered SpeI ... EcoRI ... XhoI ... EcoRI) is opened by double digestion with SpeI and XhoI. The human sEH cDNA insert in pBluescript (ordered SpeI ... EcoRI ... insert ... XhoI) is excised by digestion with SpeI and XhoI, separated by electrophoresis in low melting temperature agarose, and ligated into the mutated pBluescript plasmid. This human sEH insert in the mutated plasmid (ordered SpeI ... EcoRI ... insert ... XhoI ... EcoRI) is excised by digestion with EcoRI, and ligated into the EcoRI site of plasmid pAcUW21 forming the baculovirus cotransfection plasmid pAcUW21-hsEH. The plasmid pAcUW21 is described by Bishop, D. H. L. in *Seminars in Virology*, 3:253–264, (1992).

To obtain recombinant baculovirus, *Spodoptera frugiperda* 21 (Sf21) insect cells are cotransfected with plasmid pAcUW21-hsEH plus linearized DNA (AcRP6-SC) of *Autographa californica* nuclear polyhedrosis virus (AcNPV). *Autographa californica* nuclear polyhedrosis virus is describe in more detail by Kitts, P. A., et al., in *Nucleic Acid Res.*, 18:5667–5672, (1990). The resulting virus plaque is purified as described by O'Reilly, D. R., et al., in *Baculovirus Expresssion Vectors. A Labortory Manual*, p. 347, W. H. Freeman & Company, New York (1992). Cultures of Sf21 cells are then infected with recombinant AcNPV containing the human sEH sequence or with control AcNPV. Uninfected cultures are also maintained. Cultures are maintained 4 to 5 days post infection before harvesting proteins. For extraction of proteins, cells are washed (three times in 90 mM NaHPO$_4$ pH7.4) then lysed (in 90 mM NaHPO$_4$ pH7.4, 1 mM EDTA, 1 mM phenylmethylsulfonyl fluoride) by 3 cycles of freeze thawing (dry ice ethanol and 37° C. H$_2$O baths). Lysates are centrifuged for 3 min at 14,000×g, and the supernatant assayed for protein concentration (Pierce Bicinchoninic acid reagent) and for epoxide hydrolytic activity using [$^3$H]trans-stilbene oxide (TSO) and [$^3$H]cis-stilbene oxide (CSO) as described by Wixtrom, R. N., et al., in *Biochemical Pharamcology and Toxicity*, Vol. 1: Methodological Aspects of Drug Metabolizing Enzymes (Zakim, D. and Vessey, D. A., eds) 1, pp. 1–93, John Wiley & Sons, Inc., New York, (1985).

d) Characterization of recombinant human sEH
i) assay of enzyme inhibition

The phenylglycidol compounds (2R,3R)-3-(4-nitrophenyl) glycidol (RRNPG) and (2S,3S)-3-(4-nitrophenyl) glycidol (SSNPG) inhibit sEH of various species (mouse, rabbit, primate) enantioselectively, with I$_{50}$ values for SSNPG and RRNPG of 1 to 10 μM and >690 μ M, respectively, as described by Dietze, E. C., et al. in *Biochem. Pharmacol.*, 42:1163–1175 (1991) and by Dietze, E. C., et al., in *Comp. Biochem. Physiol.* vol.305 (1993).

Table II shows the results of inhibition experiments where preincubation of lysates (from human sEH expressing cells) with SSNPG were inhibited 73% of the hydrolysis of TSO and CSO, while preincubation with RRNPG were inhibited 39% of TSO and CSO hydrolysis. 4-fluorochalcone oxide (4FCO) is a very selective inhibitor of sEH and inhibits only very weakly other enzymes that catalyze the hydrolysis or conjugation of epoxides as reported by Mullin, C. A., and B. D. Hammock in *Arch. Biochem. Biophys.*, 216:423–439 (1982), and by Prestwich, G. D., et al., in *Arch. Biochem. Biophys.* 242:11–15, (1985). Preincubation of expressed human sEH with 4FCO inhibited 100% of the activity of hsEH (Table II). To demonstrate heat lability, the enzyme assay mixture was preincubated for 15 min at 65° C. prior to assaying for activity. The expressed human sEH was inhibited 100%.

TABLE II

Human soluble EH activity in Sf21 cells
Values are means (± standard deviation) of assays performed in triplicate. Values are specific activities in nmoles TSO or CSO converted to diol * mg$^{-1}$ * min$^{-1}$. The specific activity reported for human liver cytosol is less than 2.0.

| cells, infected with | Inhibitor (62.5 μM) | Substrates | |
|---|---|---|---|
| | | TSO | CSO |
| uninfected | none | ND$^{(a)}$ | ND |
| control virus | none | ND | ND |
| AchsEH1 | none | 21.4 (1.2) | 32.6 (0.2) |
| AchsEH1 | 4FCO | ND | ND |
| AchsEH1 | RRNPG | 13.0 (0.76) | 19.8 (1.26) |

TABLE II-continued

Human soluble EH activity in Sf21 cells
Values are means (± standard deviation) of assays performed in triplicate. Values are specific activities in nmoles TSO or CSO converted to diol * mg$^{-1}$ * min$^{-1}$. The specific activity reported for human liver cytosol is less than 2.0.

| cells, infected with | Inhibitor (62.5 μM) | Substrates TSO | CSO |
| --- | --- | --- | --- |
| AchsEH1 | SSNPG | 5.73 (0.56) | 8.72 (0.40) |

(a)ND indicates no activity was detected under conditions where rates of 0.65 nmoles * mg$^{-1}$ * min$^{-1}$ were distinguishable above background.

ii) Western transfer analysis

Human liver cytosol was prepared as the 100,000×g supernatant as described by Gill, S. S., in *Biochem. Biophys. Res. Commun.*, 112:763–769, (1983). To separate proteins by SDS-PAGE, protein samples (20 μg from cell cultures, 60 μg from human liver cytosol) were run on 10% gels then either stained with Coomassie Brilliant Blue or electrotransferred to nitrocellulose for Western analysis using rabbit antibodies raised against rhesus sEH. This antibody is described by Silva, M. and B. D. Hammock in *Comp. Biochem. Physiol.*, 87B:95–102, (1987). The Western analysis was done according to Sambrook, et al. supra.

The proteins of cell lysates from control and AchsEH1 transfected cells and human liver cytosol were separated by SDS-PAGE then stained or subjected to Western blot analysis. The stained gel shows a visible band from the insect cells infected with recombinant AcNPV containing the human sEH sequence cells which migrates as the expected mass (58–62 kDa) for human sEH. This band is not visible in the lanes containing equal amounts of proteins from control cells. Western blot analysis indicates immunoreactivity between anti-sEH antibodies and similarly migrating proteins (60 kDa) from human cytosol and the insect cells infected with recombinant AcNPV containing the human sEH sequence. The anti-rhesus sEH antibody used is found to be selectively reactive with rhesus, baboon, and human sEH, both in crude cytosol as well as apparently homogeneous protein following affinity chromatography.

What is claimed is:

1. An isolated DNA sequence encoding a human soluble epoxide hydrolase of about 62,640 daltons, wherein said human soluble epoxide hydrolase catalyzes the hydrolysis of an epoxide, said sequence specifically hybridizing to Seq. ID No.: 1 and its corresponding gene under stringent conditions, said hybridization taking place in the presence of a human DNA sequence library.

2. A DNA sequence of claim 1 wherein the soluble epoxide hydrolase has the amino acid sequence of Seq. ID No.: 2.

3. A DNA sequence of claim 2 contained in a recombinant vector.

4. A DNA sequence of claim 3 wherein said vector is capable of replicating in a prokaryotic or eukaryotic organism.

5. A DNA sequence of claim 4 wherein said prokaryotic organism is selected from the group consisting of *E. coli, Bacillus sp.,* or *S. typhimurium.*

6. A DNA sequence of claim 4 wherein said eukaryotic organism is maintained as a cell line selected from the group consisting of yeast, insect, or mammalian.

7. A DNA of claim 6 wherein said mammalian organism is maintained as a cell line selected from the group consisting of VERO, HeLa, Chinese hamster ovary, WI38, BHK, COS, or MDCK.

8. A DNA of claim 3 wherein said vector is an expression vector, said expression vector containing said DNA encoding said human soluble epoxide hydrolase operably linked to an expression control sequence.

9. A DNA of claim 8 wherein said expression vector is capable of expressing said soluble epoxide hydrolase in a prokaryotic or eukaryotic organism.

10. A DNA sequence of claim 9 wherein said prokaryotic organism is selected from the group consisting of *E. coli, Bacillus sp.,* or *S. typhimurium.*

11. A DNA sequence of claim 9 wherein said eukaryotic organism is maintained as a cell line selected from the group consisting of yeast, insect, or mammalian.

12. A DNA of claim 11 wherein said mammalian organism is maintained as a cell line selected from the group consisting of VERO, HeLa, Chinese hamster ovary, WI38, BHK, COS, or MDCK.

13. A DNA of claim 11 wherein said insect cell line is derived from *Spodoptera frugiperda* 21 (Sf21).

14. A DNA of claim 13 wherein said expression vector is a recombinant *Autographa californica* nuclear polyhedrosis virus.

15. An expression vector comprising an isolated DNA sequence encoding a human soluble epoxide hydrolase of about 62,640 daltons operably linked to an expression control sequence, said isolated DNA sequence specifically hybridizing to Seq. ID No.:1 and its corresponding gene under stringent conditions, said hybridization taking place in the presence of a human DNA sequence library.

16. A method of producing a human soluble epoxide hydrolase protein of about 62,400 daltons, wherein said human soluble epoxide hydrolase protein catalyzes the hydrolysis of an epoxide, which comprises: (a) growing a culture of a microorganism harboring an expression vector having inserted therein an isolated DNA sequence encoding a human soluble epoxide hydrolase operably linked to an expression control sequence, said DNA sequence specifically hybridizing to Seq. ID No.: 1 and its corresponding gene under stringent conditions, said hybridization taking place in the presence of a human DNA sequence library, (b) expressing said soluble epoxide hydrolase from said expression vector, and recovering said protein therefrom.

17. The method of claim 16 wherein said expression vector is capable of expressing said soluble epoxide hydrolase in a prokaryotic or eukaryotic organism.

18. A method of claim 17 wherein said prokaryotic organism is selected from the group consisting of *E. coli, Bacillus sp.,* or *S. typhimurium.*

19. A method of claim 17 wherein said eukaryotic organism is maintained as a cell line selected from the group consisting of yeast, insect, or mammalian.

20. A method of claim 19 wherein said mammalian organism is maintained as a cell line selected from the group consisting of VERO, HeLa, Chinese hamster ovary, WI38, BHK, COS, or MDCK.

21. A method of claim 19 wherein said insect cell line is derived from *Spodoptera frugiperda* 21 (Sf21).

22. A method of claim 21 wherein said expression vector is a recombinant *Autographa californica* nuclear polyhedrosis virus.

* * * * *

UNITED STATES PATENT AND TRADEMARK OFFICE
CERTIFICATE OF CORRECTION

PATENT NO.  : 5,445,956

DATED       : August 29, 1995

INVENTOR(S) : Bruce D. Hammock, David F. Grant and Jeffrey K. Beetham

It is certified that error appears in the above-identified patent and that said Letters Patent is hereby corrected as shown below:

in Claim 16 at column 40, line 15, change "62,400" to --62,640--;

Signed and Sealed this

Twenty-seventh Day of February, 1996

Attest:

BRUCE LEHMAN

*Attesting Officer*          *Commissioner of Patents and Trademarks*

UNITED STATES PATENT AND TRADEMARK OFFICE
CERTIFICATE OF CORRECTION

PATENT NO. : 5,445,956  
APPLICATION NO. : 08/106761  
DATED : August 29, 1995  
INVENTOR(S) : Hammock et al.

Page 1 of 1

It is certified that error appears in the above-identified patent and that said Letters Patent is hereby corrected as shown below:

At Column 1, Line 3, under the title of the invention, please insert the following:

-- STATEMENT AS TO RIGHTS TO INVENTIONS MADE UNDER FEDERALLY SPONSORED RESEARCH OR DEVELOPMENT

This invention was made with Government support under contract ES-02710 awarded by the National Institutes of Health. The Government has certain rights in this invention. --

Signed and Sealed this

Twenty-second Day of June, 2010

David J. Kappos
*Director of the United States Patent and Trademark Office*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 2101 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( i x ) FEATURE:
        ( A ) NAME/KEY: CDS
        ( B ) LOCATION: 42..1703

( x i ) SEQUENCE DESCRIPTION: SEQ ID NO:1:

```
GGCACGAGCT CTCTCTCTCT CTCTCTCTCT CTCTCGCCGC C ATG ACG CTG CGC                    53
                                             Met Thr Leu Arg
                                              1

GGC GCC GTC TTC GAC CTT GAC GGG GTG CTG GCG CTG CCA GCG GTG TTC                 101
Gly Ala Val Phe Asp Leu Asp Gly Val Leu Ala Leu Pro Ala Val Phe
 5               10                  15                  20

GGC GTC CTC GGC CGC ACG GAG GAG GCC CTG GCG CTG CCC AGA GGA CTT                 149
Gly Val Leu Gly Arg Thr Glu Glu Ala Leu Ala Leu Pro Arg Gly Leu
                 25                  30                  35

CTG AAT GAT GCT TTC CAG AAA GGG GGA CCA GAG GGT GCC ACT ACC CGG                 197
Leu Asn Asp Ala Phe Gln Lys Gly Gly Pro Glu Gly Ala Thr Thr Arg
                 40                  45                  50

CTT ATG AAA GGA GAG ATC ACA CTT TCC CAG TGG ATA CCA CTC ATG GAA                 245
Leu Met Lys Gly Glu Ile Thr Leu Ser Gln Trp Ile Pro Leu Met Glu
     55                  60                  65

GAA AAC TGC AGG AAG TGC TCC GAG ACC GCT AAA GTC TGC CTC CCC AAG                 293
Glu Asn Cys Arg Lys Cys Ser Glu Thr Ala Lys Val Cys Leu Pro Lys
     70                  75                  80

AAT TTC TCC ATA AAA GAA ATC TTT GAC AAG GCG ATT TCA GCC AGA AAG                 341
Asn Phe Ser Ile Lys Glu Ile Phe Asp Lys Ala Ile Ser Ala Arg Lys
 85                  90                  95                 100
```

| | | | | | | | | | | | | | | | | |
|---|---|---|---|---|---|---|---|---|---|---|---|---|---|---|---|---|
| ATC | AAC | CGC | CCC | ATG | CTC | CAG | GCA | GCT | CTC | ATG | CTC | AGG | AAG | AAA | GGA | 389 |
| Ile | Asn | Arg | Pro | Met | Leu | Gln | Ala | Ala | Leu | Met | Leu | Arg | Lys | Lys | Gly | |
| | | | | 105 | | | | | 110 | | | | | 115 | | |
| TTC | ACT | ACT | GCC | ATC | CTC | ACC | AAC | ACC | TGG | CTG | GAC | GAC | CGT | GCT | GAG | 437 |
| Phe | Thr | Thr | Ala | Ile | Leu | Thr | Asn | Thr | Trp | Leu | Asp | Asp | Arg | Ala | Glu | |
| | | | 120 | | | | | 125 | | | | | 130 | | | |
| AGA | GAT | GGC | CTG | GCC | CAG | CTG | ATG | TGT | GAG | CTG | AAG | ATG | CAC | TTT | GAC | 485 |
| Arg | Asp | Gly | Leu | Ala | Gln | Leu | Met | Cys | Glu | Leu | Lys | Met | His | Phe | Asp | |
| | | 135 | | | | | 140 | | | | | 145 | | | | |
| TTC | CTG | ATA | GAG | TCG | TGT | CAG | GTG | GGA | ATG | GTC | AAA | CCT | GAA | CCT | CAG | 533 |
| Phe | Leu | Ile | Glu | Ser | Cys | Gln | Val | Gly | Met | Val | Lys | Pro | Glu | Pro | Gln | |
| | 150 | | | | | 155 | | | | | 160 | | | | | |
| ATC | TAC | AAG | TTT | CTG | CTG | GAC | ACC | CTG | AAG | GCC | AGC | CCC | AGT | GAG | GTC | 581 |
| Ile | Tyr | Lys | Phe | Leu | Leu | Asp | Thr | Leu | Lys | Ala | Ser | Pro | Ser | Glu | Val | |
| 165 | | | | | 170 | | | | | 175 | | | | | 180 | |
| GTT | TTT | TTG | GAT | GAC | ATC | GGG | GCT | AAT | CTG | AAG | CCA | GCC | CGT | GAC | TTG | 629 |
| Val | Phe | Leu | Asp | Asp | Ile | Gly | Ala | Asn | Leu | Lys | Pro | Ala | Arg | Asp | Leu | |
| | | | | 185 | | | | | 190 | | | | | 195 | | |
| GGA | ATG | GTC | ACC | ATC | CTG | GTC | CAG | GAC | ACT | GAC | ACG | GCC | CTG | AAA | GAA | 677 |
| Gly | Met | Val | Thr | Ile | Leu | Val | Gln | Asp | Thr | Asp | Thr | Ala | Leu | Lys | Glu | |
| | | | 200 | | | | | 205 | | | | | 210 | | | |
| CTG | GAG | AAA | GTG | ACC | GGA | ATC | CAG | CTT | CTC | AAT | ACC | CCG | GCC | CCT | CTG | 725 |
| Leu | Glu | Lys | Val | Thr | Gly | Ile | Gln | Leu | Leu | Asn | Thr | Pro | Ala | Pro | Leu | |
| | | 215 | | | | | 220 | | | | | 225 | | | | |
| CCG | ACC | TCT | TGC | AAT | CCA | AGT | GAC | ATG | AGC | CAT | GGG | TAC | GTG | ACA | GTA | 773 |
| Pro | Thr | Ser | Cys | Asn | Pro | Ser | Asp | Met | Ser | His | Gly | Tyr | Val | Thr | Val | |
| | 230 | | | | | 235 | | | | | 240 | | | | | |
| AAG | CCC | AGG | GTC | CGT | CTG | CAT | TTT | GTG | GAG | CTG | GGC | TGG | CCT | GCT | GTG | 821 |
| Lys | Pro | Arg | Val | Arg | Leu | His | Phe | Val | Glu | Leu | Gly | Trp | Pro | Ala | Val | |
| 245 | | | | | 250 | | | | | 255 | | | | | 260 | |
| TGC | CTC | TGC | CAT | GGA | TTT | CCC | GAG | AGT | TGG | TAT | TCT | TGG | AGG | TAC | CAG | 869 |
| Cys | Leu | Cys | His | Gly | Phe | Pro | Glu | Ser | Trp | Tyr | Ser | Trp | Arg | Tyr | Gln | |
| | | | | 265 | | | | | 270 | | | | | 275 | | |
| ATC | CCT | GCT | CTG | GCC | CAG | GCA | GGT | TAC | CGG | GTC | CTA | GCT | ATG | GAC | ATG | 917 |
| Ile | Pro | Ala | Leu | Ala | Gln | Ala | Gly | Tyr | Arg | Val | Leu | Ala | Met | Asp | Met | |
| | | | 280 | | | | | 285 | | | | | 290 | | | |
| AAA | GGC | TAT | GGA | GAG | TCA | TCT | GCT | CCT | CCC | GAA | ATA | GAA | GAA | TAT | TGC | 965 |
| Lys | Gly | Tyr | Gly | Glu | Ser | Ser | Ala | Pro | Pro | Glu | Ile | Glu | Glu | Tyr | Cys | |
| | | 295 | | | | | 300 | | | | | 305 | | | | |
| ATG | GAA | GTG | TTA | TGT | AAG | GAG | ATG | GTA | ACC | TTC | CTG | GAT | AAA | CTG | GGC | 1013 |
| Met | Glu | Val | Leu | Cys | Lys | Glu | Met | Val | Thr | Phe | Leu | Asp | Lys | Leu | Gly | |
| | 310 | | | | | 315 | | | | | 320 | | | | | |
| CTC | TCT | CAA | GCA | GTG | TTC | ATT | GGC | CAT | GAC | TGG | GGT | GGC | ATG | CTG | GTG | 1061 |
| Leu | Ser | Gln | Ala | Val | Phe | Ile | Gly | His | Asp | Trp | Gly | Gly | Met | Leu | Val | |
| 325 | | | | | 330 | | | | | 335 | | | | | 340 | |
| TGG | TAC | ATG | GCT | CTC | TTC | TAC | CCC | GAG | AGA | GTG | AGG | GCG | GTG | GCC | AGT | 1109 |
| Trp | Tyr | Met | Ala | Leu | Phe | Tyr | Pro | Glu | Arg | Val | Arg | Ala | Val | Ala | Ser | |
| | | | | 345 | | | | | 350 | | | | | 355 | | |
| TTG | AAT | ACT | CCC | TTC | ATA | CCA | GCA | AAT | CCC | AAC | ATG | TCC | CCT | TTG | GAG | 1157 |
| Leu | Asn | Thr | Pro | Phe | Ile | Pro | Ala | Asn | Pro | Asn | Met | Ser | Pro | Leu | Glu | |
| | | | 360 | | | | | 365 | | | | | 370 | | | |
| AGT | ATC | AAA | GCC | AAC | CCA | GTA | TTT | GAT | TAC | CAG | CTC | TAC | TTC | CAA | GAA | 1205 |
| Ser | Ile | Lys | Ala | Asn | Pro | Val | Phe | Asp | Tyr | Gln | Leu | Tyr | Phe | Gln | Glu | |
| | | 375 | | | | | 380 | | | | | 385 | | | | |
| CCA | GGA | GTG | GCT | GAG | GCT | GAA | CTG | GAA | CAG | AAC | CTG | AGT | CGG | ACT | TTC | 1253 |
| Pro | Gly | Val | Ala | Glu | Ala | Glu | Leu | Glu | Gln | Asn | Leu | Ser | Arg | Thr | Phe | |
| | 390 | | | | | 395 | | | | | 400 | | | | | |
| AAA | AGC | CTC | TTC | AGA | GCA | AGC | GAT | GAG | AGT | GTT | TTA | TCC | ATG | CAT | AAA | 1301 |
| Lys | Ser | Leu | Phe | Arg | Ala | Ser | Asp | Glu | Ser | Val | Leu | Ser | Met | His | Lys | |
| 405 | | | | | 410 | | | | | 415 | | | | | 420 | |
| GTC | TGT | GAA | GCG | GGA | GGA | CTT | TTT | GTA | AAT | AGC | CCA | GAA | GAG | CCC | AGC | 1349 |

|  |  |  |  |  |  |  |  |  |  |  |  |  |  |  |  |
|---|---|---|---|---|---|---|---|---|---|---|---|---|---|---|---|
| Val | Cys | Glu | Ala | Gly<br>425 | Gly | Leu | Phe | Val | Asn<br>430 | Ser | Pro | Glu | Glu | Pro<br>435 | Ser |
| CTC | AGC | AGG | ATG | GTC | ACT | GAG | GAG | GAA | ATC | CAG | TTC | TAT | GTG | CAG | CAG |
| Leu | Ser | Arg | Met<br>440 | Val | Thr | Glu | Glu | Ile<br>445 | Gln | Phe | Tyr | Val<br>450 | Gln | Gln | |
| TTC | AAG | AAG | TCT | GGT | TTC | AGA | GGT | CCT | CTA | AAC | TGG | TAC | CGA | AAC | ATG |
| Phe | Lys | Lys<br>455 | Ser | Gly | Phe | Arg | Gly<br>460 | Pro | Leu | Asn | Trp | Tyr<br>465 | Arg | Asn | Met |
| GAA | AGG | AAC | TGG | AAG | TGG | GCT | TGC | AAA | AGC | TTG | GGA | CGG | AAG | ATC | CTG |
| Glu | Arg | Asn<br>470 | Trp | Lys | Trp | Ala<br>475 | Cys | Lys | Ser | Leu | Gly<br>480 | Arg | Lys | Ile | Leu |
| ATT | CCG | GCC | CTG | ATG | GTC | ACG | GCG | GAG | AAG | GAC | TTC | GTG | CTC | GTT | CCT |
| Ile<br>485 | Pro | Ala | Leu | Met | Val<br>490 | Thr | Ala | Glu | Lys<br>495 | Asp | Phe | Val | Leu | Val | Pro<br>500 |
| CAG | ATG | TCC | CAG | CAC | ATG | GAG | GAC | TGG | ATT | CCC | CAC | CTG | AAA | AGG | GGA |
| Gln | Met | Ser | Gln | His<br>505 | Met | Glu | Asp | Trp | Ile<br>510 | Pro | His | Leu | Lys | Arg<br>515 | Gly |
| CAC | ATT | GAG | GAC | TGT | GGG | CAC | TGG | ACA | CAG | ATG | GAC | AAG | CCA | ACC | GAG |
| His | Ile | Glu | Asp<br>520 | Cys | Gly | His | Trp | Thr<br>525 | Gln | Met | Asp | Lys<br>530 | Pro | Thr | Glu |
| GTG | AAT | CAG | ATC | CTC | ATT | AAG | TGG | CTG | GAT | TCT | GAT | GCC | CGG | AAC | CCA |
| Val | Asn | Gln<br>535 | Ile | Leu | Ile | Lys | Trp<br>540 | Leu | Asp | Ser | Asp | Ala<br>545 | Arg | Asn | Pro |
| CCG | GTG | GTC | TCA | AAG | ATG | TAGAACGCAG | | CGTAGTGCCC | | ACGCTCAGCA | | | | | |
| Pro | Val | Val | Ser | Lys | Met<br>550 | | | | | | | | | | |

|  |  |
|---|---|
| CTC AGC AGG ATG GTC ACT GAG GAG GAA ATC CAG TTC TAT GTG CAG CAG | 1397 |
| TTC AAG AAG TCT GGT TTC AGA GGT CCT CTA AAC TGG TAC CGA AAC ATG | 1445 |
| GAA AGG AAC TGG AAG TGG GCT TGC AAA AGC TTG GGA CGG AAG ATC CTG | 1493 |
| ATT CCG GCC CTG ATG GTC ACG GCG GAG AAG GAC TTC GTG CTC GTT CCT | 1541 |
| CAG ATG TCC CAG CAC ATG GAG GAC TGG ATT CCC CAC CTG AAA AGG GGA | 1589 |
| CAC ATT GAG GAC TGT GGG CAC TGG ACA CAG ATG GAC AAG CCA ACC GAG | 1637 |
| GTG AAT CAG ATC CTC ATT AAG TGG CTG GAT TCT GAT GCC CGG AAC CCA | 1685 |
| CCG GTG GTC TCA AAG ATG TAGAACGCAG CGTAGTGCCC ACGCTCAGCA | 1733 |
| GGTGTGCCAT CCTTCCACCT GCTGGGGCAC CATTCTTAGT ATACAGAGGT GGCCTTACAC | 1793 |
| ACATCTTGCA TGGATGGCAG CATTGTTCTG AAGGGGTTTG CAGAAAAAAA AGATTTTCTT | 1853 |
| TACATAAAGT GAATCAAATT TGACATTATT TTAGATCCCA GAGAAATCAG GTGTGATTAG | 1913 |
| TTCTCCAGGC ATGAATGCAT CGTCCCTTTA TCTGTAAGAA CCCTTAGTGT CCTGTAGGGG | 1973 |
| GACAGAATGG GGTGGCCAGG TGGTGATTTC TCTTTGACCA ATGCATAGTT TGGCAGAAAA | 2033 |
| ATCAGCCGTT CATTTAGAAG AATCTTAGCA GAGATTGGGA TGCCTTACTC AATAAGCTA | 2093 |
| AGATGACT | 2101 |

( 2 ) INFORMATION FOR SEQ ID NO:2:

( i ) SEQUENCE CHARACTERISTICS:
        ( A ) LENGTH: 554 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met<br>1 | Thr | Leu | Arg | Gly<br>5 | Ala | Val | Phe | Asp | Leu<br>10 | Asp | Gly | Val | Leu | Ala<br>15 | Leu |
|---|---|---|---|---|---|---|---|---|---|---|---|---|---|---|---|
| Pro | Ala | Val | Phe<br>20 | Gly | Val | Leu | Gly | Arg<br>25 | Thr | Glu | Glu | Ala<br>30 | Leu | Ala | Leu |
| Pro | Arg | Gly<br>35 | Leu | Leu | Asn | Asp | Ala<br>40 | Phe | Gln | Lys | Gly | Gly<br>45 | Pro | Glu | Gly |
| Ala | Thr<br>50 | Thr | Arg | Leu | Met | Lys<br>55 | Gly | Glu | Ile | Thr | Leu<br>60 | Ser | Gln | Trp | Ile |
| Pro<br>65 | Leu | Met | Glu | Glu | Asn<br>70 | Cys | Arg | Lys | Cys | Ser<br>75 | Glu | Thr | Ala | Lys | Val<br>80 |
| Cys | Leu | Pro | Lys | Asn<br>85 | Phe | Ser | Ile | Lys | Glu<br>90 | Ile | Phe | Asp | Lys | Ala<br>95 | Ile |
| Ser | Ala | Arg | Lys<br>100 | Ile | Asn | Arg | Pro | Met<br>105 | Leu | Gln | Ala | Ala | Leu<br>110 | Met | Leu |

-continued

| | | | | | | | | | | | | | | |
|---|---|---|---|---|---|---|---|---|---|---|---|---|---|---|
|Arg|Lys|Lys 115|Gly|Phe|Thr|Thr 120|Ala|Ile|Leu|Thr|Asn 125|Thr|Trp|Leu|Asp|
|Asp|Arg 130|Ala|Glu|Arg|Asp 135|Gly|Leu|Ala|Gln|Leu 140|Met|Cys|Glu|Leu|Lys|
|Met 145|His|Phe|Asp|Phe|Leu 150|Ile|Glu|Ser|Cys|Gln 155|Val|Gly|Met|Val|Lys 160|
|Pro|Glu|Pro|Gln|Ile 165|Tyr|Lys|Phe|Leu|Leu 170|Asp|Thr|Leu|Lys|Ala 175|Ser|
|Pro|Ser|Glu|Val 180|Val|Phe|Leu|Asp|Asp 185|Ile|Gly|Ala|Asn|Leu 190|Lys|Pro|
|Ala|Arg|Asp 195|Leu|Gly|Met|Val|Thr 200|Ile|Leu|Val|Gln|Asp 205|Thr|Asp|Thr|
|Ala|Leu 210|Lys|Glu|Leu|Glu|Lys 215|Val|Thr|Gly|Ile|Gln 220|Leu|Leu|Asn|Thr|
|Pro 225|Ala|Pro|Leu|Pro|Thr 230|Ser|Cys|Asn|Pro|Ser 235|Asp|Met|Ser|His|Gly 240|
|Tyr|Val|Thr|Val|Lys 245|Pro|Arg|Val|Arg|Leu 250|His|Phe|Val|Glu|Leu 255|Gly|
|Trp|Pro|Ala|Val 260|Cys|Leu|Cys|His|Gly 265|Phe|Pro|Glu|Ser|Trp 270|Tyr|Ser|
|Trp|Arg|Tyr 275|Gln|Ile|Pro|Ala|Leu 280|Ala|Gln|Ala|Gly|Tyr 285|Arg|Val|Leu|
|Ala|Met 290|Asp|Met|Lys|Gly|Tyr 295|Gly|Glu|Ser|Ser|Ala 300|Pro|Pro|Glu|Ile|
|Glu 305|Glu|Tyr|Cys|Met|Glu 310|Val|Leu|Cys|Lys|Glu 315|Met|Val|Thr|Phe|Leu 320|
|Asp|Lys|Leu|Gly|Leu 325|Ser|Gln|Ala|Val|Phe 330|Ile|Gly|His|Asp|Trp 335|Gly|
|Gly|Met|Leu|Val 340|Trp|Tyr|Met|Ala|Leu 345|Phe|Tyr|Pro|Glu|Arg 350|Val|Arg|
|Ala|Val|Ala 355|Ser|Leu|Asn|Thr|Pro 360|Phe|Ile|Pro|Ala|Asn 365|Pro|Asn|Met|
|Ser|Pro 370|Leu|Glu|Ser|Ile|Lys 375|Ala|Asn|Pro|Val|Phe 380|Asp|Tyr|Gln|Leu|
|Tyr 385|Phe|Gln|Glu|Pro|Gly 390|Val|Ala|Glu|Ala|Glu 395|Leu|Glu|Gln|Asn|Leu 400|
|Ser|Arg|Thr|Phe|Lys 405|Ser|Leu|Phe|Arg|Ala 410|Ser|Asp|Glu|Ser|Val 415|Leu|
|Ser|Met|His|Lys 420|Val|Cys|Glu|Ala|Gly 425|Leu|Phe|Val|Asn|Ser 430|Pro|
|Glu|Glu|Pro|Ser 435|Leu|Ser|Arg|Met|Val 440|Thr|Glu|Glu|Ile|Gln 445|Phe|
|Tyr|Val|Gln 450|Gln|Phe|Lys|Lys|Ser 455|Gly|Phe|Arg|Gly|Pro 460|Leu|Asn|Trp|
|Tyr 465|Arg|Asn|Met|Glu|Arg 470|Asn|Trp|Lys|Trp|Ala 475|Cys|Lys|Ser|Leu|Gly 480|
|Arg|Lys|Ile|Leu|Ile 485|Pro|Ala|Leu|Met|Val 490|Thr|Ala|Glu|Lys|Asp 495|Phe|
|Val|Leu|Val|Pro 500|Gln|Met|Ser|Gln|His 505|Met|Glu|Asp|Trp|Ile 510|Pro|His|
|Leu|Lys|Arg|Gly 515|His|Ile|Glu|Asp|Cys 520|Gly|His|Trp|Thr|Gln 525|Met|Asp|
|Lys|Pro|Thr 530|Glu|Val|Asn|Gln|Ile 535|Leu|Ile|Lys|Trp|Leu 540|Asp|Ser|Asp|
|Ala|Arg|Asn|Pro|Pro|Val|Val|Ser|Lys|Met| | | | | | |

-continued ( 2 ) INFORMATION FOR SEQ ID NO:3:

( i ) SEQUENCE CHARACTERISTICS:
        ( A ) LENGTH: 1969 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: murine ( i x ) FEATURE:
        ( A ) NAME/KEY: CDS
        ( B ) LOCATION: 1..1659

( x i ) SEQUENCE DESCRIPTION: SEQ ID NO:3:

```
ATG GCG CTG CGT GTA GCC GCG TTC GAC CTT GAC GGA GTG CTG GCC CTC      48
Met Ala Leu Arg Val Ala Ala Phe Asp Leu Asp Gly Val Leu Ala Leu
 1               5                  10                  15

CCC TCT ATC GCC GGG GCT TTC CGC CGC AGC GAA GAG GCC CTG GCA CTG      96
Pro Ser Ile Ala Gly Ala Phe Arg Arg Ser Glu Glu Ala Leu Ala Leu
                20                  25                  30

CCT AGA GAC TTC CTG CTT GGT GCG TAC CAG ACG GAA TTC CCA GAG GGA     144
Pro Arg Asp Phe Leu Leu Gly Ala Tyr Gln Thr Glu Phe Pro Glu Gly
            35                  40                  45

CCC ACT GAG CAA CTC ATG AAA GGG AAG ATC ACA TTT TCG CAG TGG GTA     192
Pro Thr Glu Gln Leu Met Lys Gly Lys Ile Thr Phe Ser Gln Trp Val
        50                  55                  60

CCA CTC ATG GAT GAA AGC TAC AGG AAG TCC TCC AAA GCC TGT GGA GCC     240
Pro Leu Met Asp Glu Ser Tyr Arg Lys Ser Ser Lys Ala Cys Gly Ala
 65                 70                  75                  80

AAT CTA CCT GAG AAT TTC TCC ATA AGT CAA ATA TTC AGC CAA GCT ATG     288
Asn Leu Pro Glu Asn Phe Ser Ile Ser Gln Ile Phe Ser Gln Ala Met
                85                  90                  95

GCA GCA AGA AGC ATC AAC CGC CCC ATG CTT CAG GCA GCC ATT GCT CTC     336
Ala Ala Arg Ser Ile Asn Arg Pro Met Leu Gln Ala Ala Ile Ala Leu
               100                 105                 110

AAA AAG AAA GGA TTC ACA ACA TGC ATT GTC ACC AAC AAC TGG CTG GAC     384
Lys Lys Lys Gly Phe Thr Thr Cys Ile Val Thr Asn Asn Trp Leu Asp
           115                 120                 125

GAC GGA GAC AAG AGA GAC AGC CTG GCC CAG ATG ATG TGT GAG CTG AGC     432
Asp Gly Asp Lys Arg Asp Ser Leu Ala Gln Met Met Cys Glu Leu Ser
       130                 135                 140

CAA CAC TTT GAC TTC CTG ATA GAG TCC TGT CAG GTT GGG ATG ATC AAG     480
Gln His Phe Asp Phe Leu Ile Glu Ser Cys Gln Val Gly Met Ile Lys
145                 150                 155                 160

CCT GAG CCT CAG ATC TAC AAT TTT TTA CTG GAT ACC CTG AAG GCA AAA     528
Pro Glu Pro Gln Ile Tyr Asn Phe Leu Leu Asp Thr Leu Lys Ala Lys
                165                 170                 175

CCC AAT GAG GTT GTT TTC CTA GAT GAC TTT GGA AGT AAT CTG AAG CCA     576
Pro Asn Glu Val Val Phe Leu Asp Asp Phe Gly Ser Asn Leu Lys Pro
               180                 185                 190

GCC CGT GAC ATG GGG ATG GTT ACC ATC CTG GTC CAC AAC ACA GCC TCC     624
Ala Arg Asp Met Gly Met Val Thr Ile Leu Val His Asn Thr Ala Ser
           195                 200                 205

GCT CTG AGA GAA CTG GAG AAG GTC ACA GGG ACA CAG TTT CCT GAG GCC     672
Ala Leu Arg Glu Leu Glu Lys Val Thr Gly Thr Gln Phe Pro Glu Ala
       210                 215                 220

CCA CTG CCA GTC CCA TGC AAT CCA AAT GAC GTC AGC CAT GGA TAT GTG     720
Pro Leu Pro Val Pro Cys Asn Pro Asn Asp Val Ser His Gly Tyr Val
```

```
225                     230                     235                     240

ACA GTG AAG CCA GGG ATC CGC CTG CAT TTT GTG GAG ATG CTC TGC CCT      768
Thr Val Lys Pro Gly Ile Arg Leu His Phe Val Glu Met Leu Cys Pro
            245                     250                     255

GCC CTA TGC CTT TGC CAT GGG TTT CCT GAG AGC TGG TTT TCT TGG AGG      816
Ala Leu Cys Leu Cys His Gly Phe Pro Glu Ser Trp Phe Ser Trp Arg
            260                     265                     270

TAC CAG ATC CCT GCT CTG GCC CAG GCA GGC TTT CGT GTT CTG GCT ATA      864
Tyr Gln Ile Pro Ala Leu Ala Gln Ala Gly Phe Arg Val Leu Ala Ile
            275                     280                     285

GAC ATG AAA GGC TAT GGA GAC TCA TCT TCT CCT CCT GAA ATA GAA GAA      912
Asp Met Lys Gly Tyr Gly Asp Ser Ser Ser Pro Pro Glu Ile Glu Glu
            290                     295                     300

TAT GCC ATG GAA TTG CTG TGT AAG GAG ATG GTG ACA TTC CTG GAT AAG      960
Tyr Ala Met Glu Leu Leu Cys Lys Glu Met Val Thr Phe Leu Asp Lys
305                     310                     315                     320

CTG GGA ATC CCT CAA GCA GTG TTC ATT GGC CAT GAC TGG GCT GGT GTG     1008
Leu Gly Ile Pro Gln Ala Val Phe Ile Gly His Asp Trp Ala Gly Val
            325                     330                     335

ATG GTG TGG AAC ATG GCT CTC TTC TAC CCT GAG AGA GTG AGG GCT GTG     1056
Met Val Trp Asn Met Ala Leu Phe Tyr Pro Glu Arg Val Arg Ala Val
            340                     345                     350

GCC AGT TTG AAC ACG CCG TTT ATG CCA CCA GAT CCT GAT GTG TCT CCC     1104
Ala Ser Leu Asn Thr Pro Phe Met Pro Pro Asp Pro Asp Val Ser Pro
            355                     360                     365

ATG AAA GTT ATC CGA TCT ATC CCA GTT TTC AAT TAT CAG CTG TAC TTT     1152
Met Lys Val Ile Arg Ser Ile Pro Val Phe Asn Tyr Gln Leu Tyr Phe
        370                     375                     380

CAA GAA CCA GGA GTG GCC GAG GCT GAA CTG GAG AAG AAC ATG AGT CGG     1200
Gln Glu Pro Gly Val Ala Glu Ala Glu Leu Glu Lys Asn Met Ser Arg
385                     390                     395                     400

ACT TTC AAA AGC TTC TTC CGA GCC AGT GAT GAG ACA GGT TTC ATC GCT     1248
Thr Phe Lys Ser Phe Phe Arg Ala Ser Asp Glu Thr Gly Phe Ile Ala
                405                     410                     415

GTG CAT AAA GCC ACT GAA ATA GGG GGA ATC CTT GTG AAT ACT CCA GAA     1296
Val His Lys Ala Thr Glu Ile Gly Gly Ile Leu Val Asn Thr Pro Glu
            420                     425                     430

GAT CCC AAC CTC AGC AAA ATT ACT ACT GAG GAA GAA ATA GAG TTT TAC     1344
Asp Pro Asn Leu Ser Lys Ile Thr Thr Glu Glu Glu Ile Glu Phe Tyr
            435                     440                     445

ATA CAG CAG TTC AAG AAG ACT GGC TTC AGA GGT CCT CTG AAC TGG TAC     1392
Ile Gln Gln Phe Lys Lys Thr Gly Phe Arg Gly Pro Leu Asn Trp Tyr
        450                     455                     460

CGG AAC ACA GAA AGA AAC TGG AAG TGG AGC TGT AAA GGG TTG GGA CGA     1440
Arg Asn Thr Glu Arg Asn Trp Lys Trp Ser Cys Lys Gly Leu Gly Arg
465                     470                     475                     480

AAG ATC TTG GTC CCA GCC CTG ATG GTC ACA GCT GAG AAG GAC ATT GTA     1488
Lys Ile Leu Val Pro Ala Leu Met Val Thr Ala Glu Lys Asp Ile Val
            485                     490                     495

CTC CGT CCT GAA ATG TCC AAG AAC ATG GAA AAG TGG ATC CCT TTC CTG     1536
Leu Arg Pro Glu Met Ser Lys Asn Met Glu Lys Trp Ile Pro Phe Leu
            500                     505                     510

AAA AGG GGA CAC ATT GAA GAC TGT GGT CAC TGG ACA CAG ATA GAG AAA     1584
Lys Arg Gly His Ile Glu Asp Cys Gly His Trp Thr Gln Ile Glu Lys
        515                     520                     525

CCA ACT GAG GTG AAC CAG ATT CTC ATC AAG TGG CTG CAG ACT GAA GTC     1632
Pro Thr Glu Val Asn Gln Ile Leu Ile Lys Trp Leu Gln Thr Glu Val
        530                     535                     540

CAG AAC CCA TCA GTG ACC TCC AAG ATT TAGCCACTGG GGACACATTT           1679
Gln Asn Pro Ser Val Thr Ser Lys Ile
545                     550
```

-continued

```
TAGTTTCTGG AACACAGCCT GATCTACAAG TACCAGCATC GTTCTTTTGC CAGCCAGTGA    1739

TTTTCTTTTA AATGAAAATG ATGGGATGAG ATGTAATTTT AGATCGGGAA GAGAGTGTGT    1799

GTCTAATTCT TTTGAGTATG CCTGTGCCAT CAGAGAAGAG ATCCCACCCC AGTAGGAAGG    1859

TATGGGGCAG TCCAGTTTAT AACTTTGCAA CCAAACCCAA GCCTGCTCTT TTGAAGCAGC    1919

TGATTGGAGA GTAAAGATTT TCATTCAATA AAGCTAAACC TCAGGGCTCC               1969
```

( 2 ) INFORMATION FOR SEQ ID NO:4:

( i ) SEQUENCE CHARACTERISTICS:
        ( A ) LENGTH: 553 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ala Leu Arg Val Ala Ala Phe Asp Leu Asp Gly Val Leu Ala Leu
 1               5                  10                  15

Pro Ser Ile Ala Gly Ala Phe Arg Arg Ser Glu Glu Ala Leu Ala Leu
            20                  25                  30

Pro Arg Asp Phe Leu Leu Gly Ala Tyr Gln Thr Glu Phe Pro Glu Gly
        35                  40                  45

Pro Thr Glu Gln Leu Met Lys Gly Lys Ile Thr Phe Ser Gln Trp Val
    50                  55                  60

Pro Leu Met Asp Glu Ser Tyr Arg Lys Ser Ser Lys Ala Cys Gly Ala
65                  70                  75                  80

Asn Leu Pro Glu Asn Phe Ser Ile Ser Gln Ile Phe Ser Gln Ala Met
                85                  90                  95

Ala Ala Arg Ser Ile Asn Arg Pro Met Leu Gln Ala Ala Ile Ala Leu
            100                 105                 110

Lys Lys Lys Gly Phe Thr Thr Cys Ile Val Thr Asn Asn Trp Leu Asp
        115                 120                 125

Asp Gly Asp Lys Arg Asp Ser Leu Ala Gln Met Met Cys Glu Leu Ser
    130                 135                 140

Gln His Phe Asp Phe Leu Ile Glu Ser Cys Gln Val Gly Met Ile Lys
145                 150                 155                 160

Pro Glu Pro Gln Ile Tyr Asn Phe Leu Leu Asp Thr Leu Lys Ala Lys
                165                 170                 175

Pro Asn Glu Val Val Phe Leu Asp Asp Phe Gly Ser Asn Leu Lys Pro
            180                 185                 190

Ala Arg Asp Met Gly Met Val Thr Ile Leu Val His Asn Thr Ala Ser
        195                 200                 205

Ala Leu Arg Glu Leu Glu Lys Val Thr Gly Thr Gln Phe Pro Glu Ala
    210                 215                 220

Pro Leu Pro Val Pro Cys Asn Pro Asn Asp Val Ser His Gly Tyr Val
225                 230                 235                 240

Thr Val Lys Pro Gly Ile Arg Leu His Phe Val Glu Met Leu Cys Pro
                245                 250                 255

Ala Leu Cys Leu Cys His Gly Phe Pro Glu Ser Trp Phe Ser Trp Arg
            260                 265                 270

Tyr Gln Ile Pro Ala Leu Ala Gln Ala Gly Phe Arg Val Leu Ala Ile
        275                 280                 285

Asp Met Lys Gly Tyr Gly Asp Ser Ser Pro Pro Glu Ile Glu Glu
    290                 295                 300

Tyr Ala Met Glu Leu Leu Cys Lys Glu Met Val Thr Phe Leu Asp Lys
305                 310                 315                 320
```

| Leu | Gly | Ile | Pro | Gln 325 | Ala | Val | Phe | Ile | Gly 330 | His | Asp | Trp | Ala | Gly 335 | Val |
|-----|-----|-----|-----|-----|-----|-----|-----|-----|-----|-----|-----|-----|-----|-----|-----|
| Met | Val | Trp | Asn 340 | Met | Ala | Leu | Phe | Tyr 345 | Pro | Glu | Arg | Val | Arg 350 | Ala | Val |
| Ala | Ser | Leu 355 | Asn | Thr | Pro | Phe | Met 360 | Pro | Pro | Asp | Pro | Asp 365 | Val | Ser | Pro |
| Met | Lys 370 | Val | Ile | Arg | Ser | Ile 375 | Pro | Val | Phe | Asn | Tyr 380 | Gln | Leu | Tyr | Phe |
| Gln 385 | Glu | Pro | Gly | Val | Ala 390 | Glu | Ala | Glu | Leu | Glu 395 | Lys | Asn | Met | Ser | Arg 400 |
| Thr | Phe | Lys | Ser | Phe 405 | Phe | Arg | Ala | Ser | Asp 410 | Glu | Thr | Gly | Phe | Ile 415 | Ala |
| Val | His | Lys | Ala 420 | Thr | Glu | Ile | Gly | Gly 425 | Ile | Leu | Val | Asn | Thr 430 | Pro | Glu |
| Asp | Pro | Asn 435 | Leu | Ser | Lys | Ile | Thr 440 | Thr | Glu | Glu | Glu | Ile 445 | Glu | Phe | Tyr |
| Ile | Gln 450 | Gln | Phe | Lys | Lys | Thr 455 | Gly | Phe | Arg | Gly | Pro 460 | Leu | Asn | Trp | Tyr |
| Arg 465 | Asn | Thr | Glu | Arg | Asn 470 | Trp | Lys | Trp | Ser | Cys 475 | Lys | Gly | Leu | Gly | Arg 480 |
| Lys | Ile | Leu | Val | Pro 485 | Ala | Leu | Met | Val | Thr 490 | Ala | Glu | Lys | Asp | Ile 495 | Val |
| Leu | Arg | Pro | Glu 500 | Met | Ser | Lys | Asn | Met 505 | Glu | Lys | Trp | Ile | Pro 510 | Phe | Leu |
| Lys | Arg | Gly 515 | His | Ile | Glu | Asp | Cys 520 | Gly | His | Trp | Thr | Gln 525 | Ile | Glu | Lys |
| Pro | Thr 530 | Glu | Val | Asn | Gln | Ile 535 | Leu | Ile | Lys | Trp | Leu 540 | Gln | Thr | Glu | Val |
| Gln 545 | Asn | Pro | Ser | Val | Thr 550 | Ser | Lys | Ile | | | | | | | |

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: murine ( x i ) SEQUENCE DESCRIPTION: SEQ ID NO:5:

ATGGCGCTGC GTGTAGCCGC GTTCGACCTT      30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: murine ( x i ) SEQUENCE DESCRIPTION: SEQ ID NO:6:

TGAGGTTTAG CTTTATTGAA TGAAAATCTT                                        30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: murine ( x i ) SEQUENCE DESCRIPTION: SEQ ID NO:7:

GCCCTGGCAC TGCCTAGAGA CTTCCTGCTT                                        30

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: murine ( x i ) SEQUENCE DESCRIPTION: SEQ ID NO:8:

AATCTTGGAG GTCACTGATG GGTTCTGGAC                                        30

( 2 ) INFORMATION FOR SEQ ID NO:9:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: murine ( x i ) SEQUENCE DESCRIPTION: SEQ ID NO:9:

GGACTAGTAT GGCGCTGCGT GTAGCCGCGT TCGACCTT                               38

( 2 ) INFORMATION FOR SEQ ID NO:10:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: murine ( x i ) SEQUENCE DESCRIPTION: SEQ ID NO:10:

GGGAGCTCTG AGGTTTAGCT TTATTGAATG AAAATCTT                               38

( 2 ) INFORMATION FOR SEQ ID NO:11:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:11:

CGGAATTCAT GACGCTGCGC GGCGCCGTCT TCGACCTT    38

( 2 ) INFORMATION FOR SEQ ID NO:12:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:12:

CGAAGCTTGT AAGGCATCCC AATCTCTGCT AAGATTCT    38

( 2 ) INFORMATION FOR SEQ ID NO:13:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:13:

CGGAATTCGA CGGGGTGCTG GCGCTGCCAG CGGTGTTC    38

( 2 ) INFORMATION FOR SEQ ID NO:14:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:14:

CGAAGCTTCT ACATCTTTGA GACCACCGGT GGGTTCCG    38